United States Patent [19]

Bao et al.

[11] Patent Number: 5,047,055
[45] Date of Patent: Sep. 10, 1991

[54] HYDROGEL INTERVERTEBRAL DISC NUCLEUS

[75] Inventors: Qi-Bin Bao, Livingston; Paul A. Higham, Ringwood, both of N.J.

[73] Assignee: Pfizer Hospital Products Group, Inc., New York, N.Y.

[21] Appl. No.: 633,711

[22] Filed: Dec. 21, 1990

[51] Int. Cl.$^5$ .............................................. A61F 2/44
[52] U.S. Cl. ...................................... 623/17; 623/18; 623/901
[58] Field of Search ...................... 623/17, 18, 16, 901

[56] References Cited

U.S. PATENT DOCUMENTS

| | | | |
|---|---|---|---|
| 3,867,728 | 2/1975 | Stubstad et al. | 623/17 |
| 3,875,595 | 4/1975 | Froning | 623/17 |
| 4,309,777 | 1/1982 | Patil | 623/17 |
| 4,349,921 | 9/1982 | Kuntz | 623/17 |
| 4,714,469 | 12/1987 | Kenna | 623/17 |
| 4,772,287 | 9/1988 | Ray et al. | 623/17 |
| 4,904,260 | 2/1990 | Ray et al. | 623/17 |
| 4,911,718 | 3/1990 | Lee et al. | 623/17 |
| 4,932,969 | 6/1990 | Frey et al. | 623/17 |

FOREIGN PATENT DOCUMENTS 2639823  6/1990  France .

Primary Examiner—Ronald Frinks
Attorney, Agent, or Firm—Peter C. Richardson; Lawrence C. Akers; Raymond W. Augustin

[57] ABSTRACT

A prosthetic nucleus for a vertebral disc is made of a hydrogel material. The hydrogel prosthetic nucleus has a shape generally conforming to the natural nucleus pulposus. The hydrogel has a water content of at least 30% and has a compressive strength of 4MNm$^{-2}$ or greater. When the hydrogel material is dehydrated, it has a dimension of less than half of that of the hydrated hydrogel nucleus. The prosthetic nucleus may be formed of two or more pieces of hydrogel material which pieces, when combined, have a shape generally conforming to the natural nucleus.

10 Claims, 4 Drawing Sheets

HYDROGEL INTERVERTEBRAL DISC NUCLEUS

BACKGROUND OF THE INVENTION

1. Field of the Invention

This invention relates to a prosthetic intervertebral disc nucleus. More particularly it relates to an artificial disc nucleus made of a hydrogel material.

The intervertebral disc is a complex joint anatomically and functionally. It is composed of three component structures: the nucleus pulposus, the annulus fibrosus and the vertebral end-plates. The biomedical composition and anatomical arrangements within these component structures are related to the biomechanical function of the disc.

The nucleus pulposus occupies 25-40% of the total disc cross-sectional area. It is composed mainly of mucoid material containing mainly proteoglycans with a small amount of collagen. The proteoglycans consist of a protein core with chains of negatively charged keratin sulphate and chondroitin sulphate attached thereto. Due to these constituents, the nucleus pulposus is a "loose or amorphous hydrogel" which has the capacity to bind water and usually contains 70-90% water by weight. Although the nucleus plays an important role in the biomechanical function of the disc, the mechanical properties of the disc are not well known, largely because of the loose hydrogel nature of the nucleus.

Because the nucleus is surrounded by the annulus fibrosus and vertebral end-plates, and the negatively charged sulphate groups are immobilized due to the attachment of these groups to the polymer matrix, this causes the matrix to have a higher concentration of ions than its surroundings. This higher concentration results in a higher osmotic pressure ranging between 0.1-0.3 MPa. As a result, the high fixed charge density of the proteoglycan leads the matrix to exert an osmotic swelling pressure which can support an applied load in much the same way as air pressure in a tire supports the weight of a car.

It is the osmotic swelling pressure and hydrophilicity of the nucleus matrix that offers the nucleus the capability of imbibing fluid until it is balanced with the resistance stresses coming internally from the tensile forces of the collagen network and externally from the loads that are applied by muscle and ligament tension. The swelling pressure (Ps) of the nucleus is dependent on the concentration of proteoglycan, i.e. the higher proteoglycan concentration, the higher swelling pressure of the nucleus, and vise versa. This external pressure changes with posture. When the human body is supine, the compressure load on the third lumbar disc is 300 newtons (N), which rises to 700 N when upright stance is assumed and to 1200 N when bending forward by only 20°. When the external pressure (Pa) increases, it breaks the previous balance of Ps=Pa. To reach the new balance, the swelling pressure (Ps) has to increase. This increase is achieved by increasing the proteoglycan concentration in the nucleus which is in turn achieved by reducing the fluid in the nucleus. That is why discs will lose about 10% of their height as a result of creep during the daytime. When the external load is released (Ps>Pa), the nucleus will imbibe fluid from its surroundings in order to reach the new equilibrium. It is this property of the nucleus that is mainly responsible for the compressive properties of the disc.

The annulus fibrosus forms the outer limiting boundary of the disc. It is composed of highly structured collagen fibers embedded in amorphous base substance also composed of water and proteoglycans, which is lower in content in the annulus than in the nucleus. The collagen fibers of the annulus are arranged in concentric laminated bands (8-12 layers thick) with a thicker anterior wall and thinner posterior wall. In each lamella, the fibers are parallel and attached to the superior and inferior vertebral bodies at roughly a 30° angle from the horizontal plane of the disc in both directions. This design particularly resists twisting, as half of the angulated fibers will tighten as the vertebrae rotate relative to each other in either direction.

The composition of the annulus fibrosus along the radial axis is not uniform. There is a steady increase in the proportion of collagen from the inner to the outer annulus. This difference in composition may reflect the need of the inner and outer regions of the annulus to blend into very different tissues while maintaining the strength of the structure. Only the inner lamellae are anchored to the end-plates forming an enclosed vessel for the nucleus. The collagen network of the annulus restrains the tendency of the nucleus gel to absorb water from surrounding tissues and swell. Thus, the collagen fibers in the annulus are always in tension, and the nucleus gel is always in compression.

The two vertebral end-plates are composed of hyaline cartilage, which is a clear "glassy" tissue, and separates the disc from the adjacent vertebral bodies. This layer acts as a transitional zone between the hard, bony vertebral bodies and the soft disc. Because the intervertebral disc is avascular, most nutrients that the disc needs for metabolism are transported to the disc by diffusion through the end-plate area.

The intervertebral joint exhibits both elastic and viscous behavior. Hence, during the application of a load to the disc there will be an immediate "distortion" or "deformation" of the disc, often referred to as "instantaneous deformation". It has been reported that the major pathway by which water is lost from the disc during compression is through the cartilage end-plates. Because the permeability of the end-plates is in the range $(0.20 -0.85) \times 10^{-17}$ $m^4$ $N^{-1}$ $sec^{-1}$, it is reasonable to assume that under loading, the initial volume of the disc is constant while the load is applied. Because the natural nucleus of the disc is in the form of loose hydrogel which can be deformed easily, the extent of deformation of the disc is largely dependent on the extensibility of the annulus. It is generally believed that the hydrostatic behavior of the nucleus pulposus plays an important role in the normal static and dynamic load-sharing capability of the disc and the restoring force of stretched fibers of the annulus balances the effects of nucleus swelling pressure. Without the constraint from the annulus, nucleus annular bulging increases considerably. If the load is maintained at a constant level, a gradual change in joint height will occur as a function of time which is commonly referred to as "creep". Eventually, the creep will stabilize and the joint is said to be in "equilibrium". When the load is removed the joint will gradually "recover" to its original height before loading (the creep and relax rate depends on the amount of load applied, the permeability of the end-plates and the water binding capability of the nucleus hydrogel). The creep and relax is an essential process to pumping the fluid in and out of the disc.

Degeneration of the intervertebral disc is believed to be a common cause of final pathology and of back pain.

As the intervertebral disc ages, it undergoes degeneration. The changes that occur are such that in many respects the composition of the nucleus seems to approach that of the inner annulus fibrosus. Intervertebral disc degeneration is, at least in part, the consequence of the composition change of the nucleus. It has been found that both the molecular weight and the content of proteoglycans from the nucleus decreases with age, especially in degenerated discs, and the ratio of keratin sulphate to chondroitin sulphate in the nucleus increases. This increase in the ratio of keratin sulphate to chondroitin sulphates and decrease in proteoglycan content decreases the fixed charge density of the nucleus from 0.28 meq/ml to about 0.18-0.20 meq/ml. These changes cause the nucleus to lose its water binding capability and its swelling pressure. As a result, the nucleus becomes less hydrated, and its water content drops from over 85% in preadolescence to about 70-75% in middle age. The glycosaminoglycan content of prolapsed discs has been found to be lower, and the collagen content higher than that of normal discs of a comparable age. Discs L-4- L-5 and L-5 - S-1 are usually the most degenerated discs.

It is known that although the nucleus only has about one third of the total disc area, it takes about 70% of the total loading in a normal disc. It has been found that the load in the nucleus of moderately degenerated discs is 30% lower than in comparable normal discs. However, the vertical load on the annulus fibrosus increases by 100% in the degenerated discs. This load change is primarily caused by the structural changes of the disc as discussed above. The excess load on the annulus of the degenerated discs would cause narrowing of the disc spaces and excessive movement of the entire spinal segments. The flexibility would produce excessive movement of the collagenous fibers that, in turn, would injure the fiber attachments and cause delamination of the well organized fibers of the annulus ring. The delaminated annulus can be further weakened by stress on the annulus and in severe cases this stress will cause tearing of the annulus. This whole process is very similar to driving on a flat tire, where the reinforcement layer will eventually delaminate. Because the thickness of the annulus is not uniform, with the posterior being thinner than the anterior, the delamination and the lesion usually occur in the posterior area first.

The spinal disc may also be displaced or damaged due to trauma or a disease process. In this case and in the case of disc degeneration, the nucleus pulposus may herniate and/or protrude into the vertebral canal or intervertebral foramen, in which case it is known as a herniated or "slipped" disc. This disc may in turn press upon the spinal nerve that exits the vertebral canal through the partially obstructed foramen, causing pain or paralysis in the area of its distribution. The most frequent site of occurrence of a herniated disc is in the lower lumbar region. A disc herniation in this area often involves the inferior extremities by compressing the sciatic nerve.

There are basically three types of treatment currently being used for treating low back pain caused by injured or degenerated discs: conservative care, laminectomy and fusion. Each of these treatments has its advantages and limitations. The vast majority of patients with low back pain, especially those with first time episodes of low back pain, will get better with conservative care treatment. However, it is not necessarily true that conservative care is the most efficient and economical way to solve the low back pain problem.

Laminectomy usually gives excellent short term results in relieving the clinical symptoms by removing the herniated disc material (usually the nucleus) which is causing the low back pain either by compressing the spinal nerve or by chemical irritation. Clearly a laminectomy is not desirable from a biomechanical point of view. In the healthy disc, the nucleus takes the most compressional load and in the degenerated disc this load has been distributed more onto the annulus ring, which, as described above, causes tearing and delamination. The removal of the nucleus in a laminectomy actually causes the compressive load to be distributed further on the annulus ring, which would narrow the disc spaces. It has been reported that a long-term disc height decrease might be expected to cause irreversible osteoarthritic-like changes in the adjacent facet joint. That is why laminectomy has poor long term results and high incidence of reherniation.

Fusion generally does a good job in eliminating symptoms and stabilizing the joint. However, because the motion of the fused segment is restricted, it increases the range of motion of the adjoining vertebral discs, possibly enhancing their degenerative processes.

Because of these disadvantages, it is desirable to develop a prosthetic joint device which not only is able to replace the injured or degenerated intervertebral disc, but also can mimic the physiological and the biomechanical function of the replaced disc. Such a device would restore the function of the disc and prevent further degeneration of the surrounding tissue.

2. Description of the Prior Art

Various artificial discs are well known. U.S. Pat. No. 3,867,728 to Stubstad et al, which issued on Feb. 25, 1975, relates to a device which replaces the entire disc. This device is made by laminating vertical, horizontal or axial sheets of elastic polymer. U.S. Pat. No. 3,875,595 to Froning, dated Apr. 8, 1975, relates to a collapsible plastic bladder-like prosthesis of nucleus pulposus. Another U.S. patent relates to a prosthesis utilizing metal springs and cups (Patil, U.S. Pat. No. 4,309,777). A spinal implant comprising a rigid solid body having a porous coating on part of the surface is shown in Kenna's U.S. Pat. No. 4,714,469. An intervertebral disc prosthesis of a pair of rigid plugs to replace the disc is shown in Kuntz, U.S. Pat. No. 4,349,921. Ray et al, U.S. Pat. Nos. 4,772,287 and 4,904,260, use a pair of cylindrical prosthetic intervertebral disc capsules with or without therapeutical agents. U.S. Pat. No. 4,911,718 relates to an elastomeric disc spacer comprising three different parts; nucleus, annulus and endplates, of different materials. At the present time, none of these concepts has become a product in the spinal care market.

The main reason for the difficulty in implementing these concepts is that except for the concepts of Froning's, Kuntz's and Ray's, these prostheses call for replacing the entire natural disc, which involves numerous surgical difficulties. Secondly, the intervertebral disc is a complex joint anatomically and functionally and it is composed of three component structures, each of which has its own unique structural characteristics. To design and fabricate such a complicated prosthesis from acceptable materials which will mimic the function of the natural disc is very difficult. A problem also exists in finding a way to prevent the prosthesis from dislodging. Thirdly, even for prostheses which are only intended for replacing the nucleus, a major obstacle is finding a material which is in character similar to the natural nucleus and also is able to restore the natural function of the nucleus. Neither silicone elastomers nor thermoplastic polymers are ideal for the prosthetic nucleus due to their significant inherent characteristic differences from the natural nucleus.

This problem is not solved by Kuntz, which involves using elastic rubber plugs, and Froning and Ray, which use bladders filled with a fluid or plastic or thixotropic gel. In both the latter cases, liquid was used to fill the bladder so that the bladder membrane had to be completely sealed to prevent fluid leakage. Clearly, the prior devices would not completely restore the function of the nucleus which allows the fluid to diffuse in and out during cyclic loading to allow body fluid diffusion which provides the nutrients the disc needs.

This invention relates to a new prosthetic lumbar disc nucleus which is made from synthetic hydrogels. Hydrogels have been used in biomedical applications in various areas such as contact lenses. Among the advantages of hydrogels are that they are more biocompatible than other hydrophobic elastomers and metals. This biocompatibility is largely due to the unique characteristics of hydrogels in that they are soft and hydrated like the surrounding tissues and have relatively low friction with respect to the surrounding tissues. The biocompatibility of hydrogels results in a prosthetic nucleus more easily tolerated in the body.

An additional advantage is that some hydrogels have good mechanical strength which permits them to withstand the load on the disc and restore the normal space between the vertebral body. The prosthetic nucleus of the present invention has high mechanical strength and is able to withstand the body load and assist in the healing of the defective annulus.

Another advantage of the present invention is that many hydrogels have excellent visco-elastic properties and shape memory. Unlike other elastomeric polymers, hydrogels contain a large portion of water which acts as a plasticizer. Part of the water in the hydrogel is available as free water, which has more freedom to leave the hydrogel when the hydrogel is partially dehydrated or under mechanical pressure. This characteristic of the hydrogels enables them to creep in the same way as the natural nucleus under compression and to withstand cyclic loading for long periods without any significant degradation and without losing their elasticity. This is because water in the hydrogel behaves like a cushion which makes the network of the hydrogel less stretched.

In addition, hydrogels are permeable to water and water-soluble substances, such as nutrients, metabolites and the like. It is known that body fluid diffusions under cyclic loading is the major source of nutrients to the disc and if the route of this nutrient diffusion is blocked, it will cause further deterioration of the disc.

The hydrogels used in the disc of the present invention, as with many hydrogels, can be dehydrated and then hydrated again without changing the properties of the hydrogel. When the hydrogel is dehydrated, its volume will decrease, which makes it possible to implant the prosthetic nucleus in the dehydrated or unhydrated state. The implanted prosthetic nucleus will then swell slowly in the body. This feature makes it possible to implant the device laterally during surgery, thereby reducing the complexity and risk of intraspinal surgery traditionally used. The danger of perforation of the nerve, dural sac, arteries and other organs is reduced. The incision area on the annulus also can be reduced, thereby helping the healing of the annulus and preventing the reherniation of the disc. Hydrogels have also been used in drug delivery due to their capability for a controllable release of the drug. Different therapeutic agents, such as different growth factors, long term analgesics and antiinflammatory agents can be attached to the prosthetic nucleus and be released in a controllable rate after implantation.

Furthermore, dimensional integrity is maintained with hydrogels having a water content of up to 90%. This dimensional integrity, if properly designed, distributes the load to a larger area on the annulus ring and prevents the prosthetic nucleus from bulging and herniating.

SUMMARY OF THE INVENTION

It is an object of the invention to provide a prosthetic nucleus for a disc which functions in a manner very similar to the natural nucleus.

It is yet another object of the invention to provide a prosthetic nucleus for a disc which is composed of a hydrogel material capable of balancing its hydrostatic pressure with external loads thereon.

These and other objects of the present invention are disclosed in a preferred embodiment of the invention which includes a prosthetic nucleus for a disc which is composed of a hydrogel material. The hydrogel prosthetic nucleus has a shape and size generally conforming to the natural nucleus which has been removed in a regular discectomy procedure and has a water content of at least 30%, preferably 70-85%, with a compressive strength of at least 4 Meganewton per square meter ($MNm^{-2}$) or greater when hydrated to its equilibrium water content. While the preferred nucleus may have a water content of 70% to 85% when fully hydrated, it may have a water content of up to 90%.

The expansion factor of a dehydrated hydrogel will be dependent on the equilibrium water content (EWC) of that hydrogel. It may vary from 1.19 for a hydrogel of 38% EWC to 1.73 for a hydrogel of 80% EWC. For an 80% EWC hydrogel, the volume of the dehydrated prosthetic nucleus is only about 20% of the hydrated one.

After hydration in the disc, the hydrogel nucleus will be constrained tightly in the cavity from which the nucleus has been excised. The constraining forces are the restoring force of the stretched fibers of the annulus and the external force through the end-plates. The constraint from the annulus and the endplates will restrict the movement of the hydrogel nucleus and prevent it from bulging and herniating from the cavity.

The prosthetic nucleus may be formed from two or more pieces of hydrogel material, each shaped so that when combined they have a shape generally conforming to the natural nucleus. Utilizing a two-piece prosthetic nucleus facilitates implantation, which is done with the hydrogel material in a dehydrated or unhydrated state.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings wherein similar reference characters denote similar elements throughout the several views, in which.

DESCRIPTION OF THE PREFERRED EMBODIMENT

Referring to FIGS. 1 through 6, in the preferred embodiment the prosthetic nucleus of the present invention generally denoted as 10 is shaped to conform, when hydrated, to the general shape of the natural nucleus. The nucleus is implanted in disc 12 of vertebrae 14 and is surrounded by the natural annulus fibrosus 16. Vertebral end plates 20 and 22 cover the superior and inferior faces of nucleus 10 respectively. The preferred material of nucleus 10 is a hydrogel material, preferably highly hydrolysed polyvinyl alcohol (PVA). The amount of hydrolization may be between 95 and 100 percent depending on the preferred final water content desired which is about 70% to 85%. Generally, the final hydrogel water content increases as the percent of hydrolization of the initial PVA decreases.

EXAMPLE

The general technique of preparing PVA hydrogel from the commercially available PVA powder has been disclosed in the U.S. Pat. No. 4,663,358, the teachings of which are incorporated herein by reference. Typically, 10-25% PVA powder is mixed with a solvent, such as water, dimethyl sulfoxide, ethylene glycol or a mixture thereof. The slurry is then heated until a uniform gel is formed. The gel is then poured or injected into either a metal or a plastic mold which will give the shape and the size of the prosthetic nucleus. After cooling the gel below $-10°$ C. for crystallization for several hours, the shaped PVA gel will be soaked with water until all the organic solvent has been exchanged with water. The hydrated PVA gel can then be dehydrated for implantation. The PVA hydrogels thus prepared will have a water content between 60-90% and compressive strength greater than 4 $MNm^{-2}$.

While PVA is used in the preferred prosthetic disc, other hydrogels such as lightly cross-linked polymers of 2-hydroxyethyl methacrylate, or copolymers and terpolymers made from the combination of the monomers of an N-vinyl monomer, (for example, N-vinyl-2-pyrolidone (N-VP)), a hydroxy alkyl methacrylate ester, (for example, 2-hydroxylethyl methacrylate (HEMA)), an alkyl methacrylate (for example, methyl methacrylate (MMA)), an ethylenically unsaturated acid (for example, methacrylic acid (MA)) and an ethylenically unsaturated base (for example, N,N-diethylamino ethyl methacrylate (DEAEMA)) may be used.

HYPAN ™ (hydrogel polyacrylonitrile) is another type of hydrogel which can be used as a hydrogel nucleus. This hydrogel, unlike the cross-linked hydrogel, has a multiblock copolymer (MBC) structure with hard crystalline nitrile blocks which gives the hydrogel good mechanical properties and soft amorphous hydrophilic blocks which gives the hydrogel good water binding capability. The methods of preparing the HYPAN ™ hydrogels of different water contents and different mechanical properties have been disclosed in the U.S. Pat. Nos. 4,337,327, 4,370,451, 4,331,783, 4,369,294, 4,420,589, 4,379,874 and 4,631,188. The device of this material can be either melt compressed as thermoplasts or injection molded.

In general, any hydrogel that can be used for soft contact lenses can be used as long as the hydrogel exhibits a compressive strength of at least 4 $MNm^{-2}$. Most of these materials have been FDA approved for use as contact lenses. Of course, many other hydrogel compositions may be used since, unlike contact lenses, opaque materials are acceptable. The art of preparing these polymers and copolymers has been disclosed in numerous U.S. patents. The water content of these hydrogels can vary from 38% for polymacon (poly HEMA) to 79% for lidofilcon B (copolymer of N-VP and MMA).

A prosthetic nucleus made from these hydrogels can be prepared either by cast molding or lathe cutting. In cast molding, the liquid monomer mixture with initiator is poured into a mold of the predetermined shape and size. It is then cured in the mold. In the case of lathe cutting, the polymer can be prepared in a similar manner in the form of a block or rod which is larger than the prosthetic nucleus. The polymer then will be cut to the shape and size of the nucleus. In both cases, the hydrogel expansion factor due to polymer swelling upon hydration has to be taken into account in designing the mold or in cutting the prosthetic nucleus.

Figure 1:
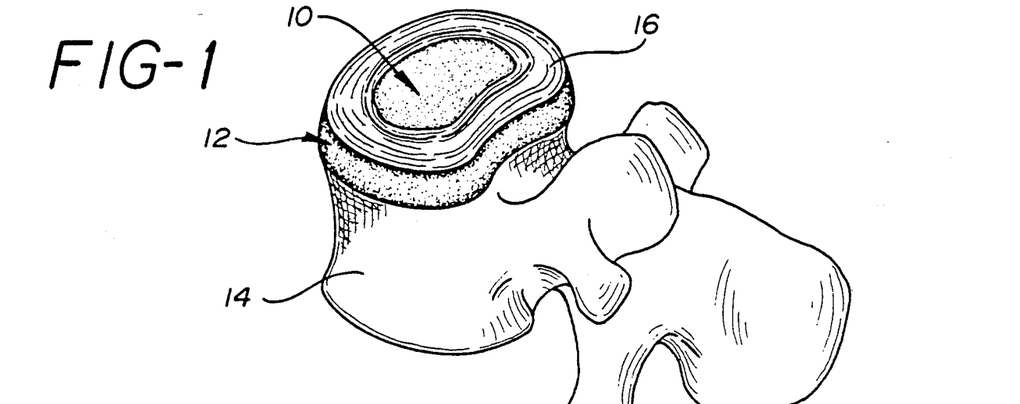
FIG. 1 is an isometric view of a single vertebral disc with the nucleus exposed.
Figure 2:
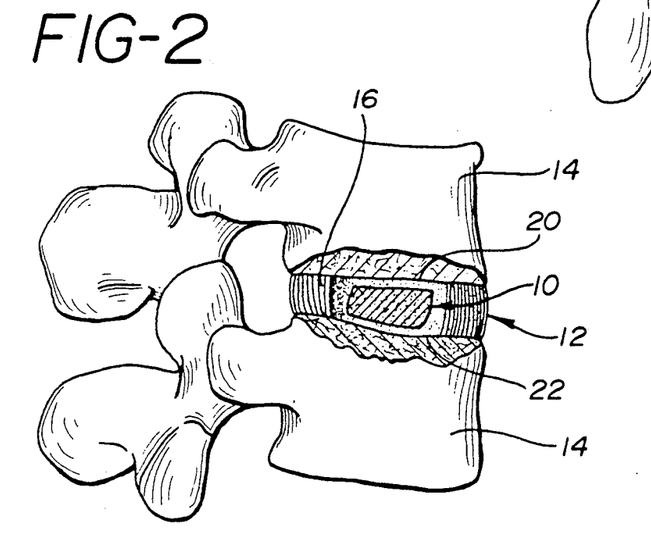
FIG. 2 is an elevation view, partially in cross-section, of a disc with the prosthetic nucleus of the present invention shown in the dehydrated state.
Figure 3:
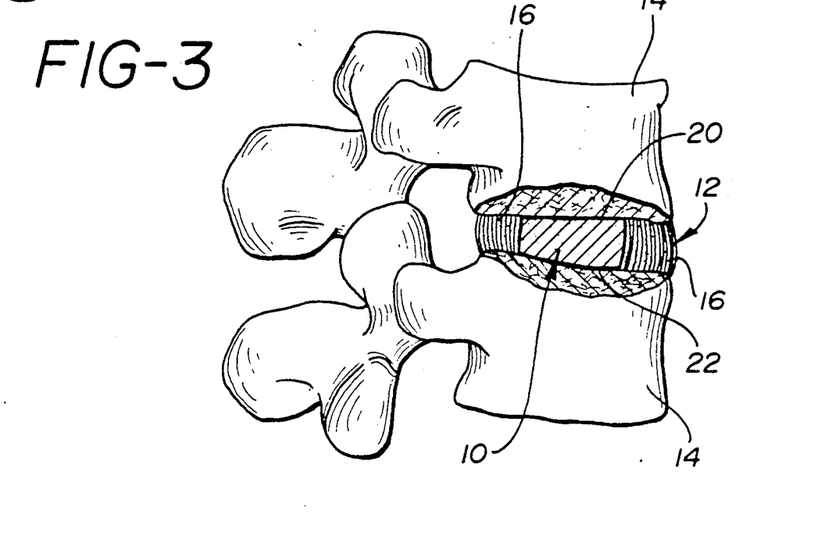
FIG. 3 is the disc of FIG. 2 showing the prosthetic nucleus of the present invention in the hydrated state.

Prosthetic nuclei 10 of various shapes can be designed as required to restore the function of the degenerated disc. In the preferred embodiment, the prosthetic nucleus approximates the shape and size of the natural nucleus, resembling an eclipse as shown in FIG. 1. The exact size of the hydrated prosthetic nucleus can be varied for different individuals. A typical size of adult nucleus is 2 cm in semi-minor axis and 4 cm in semi-major axis and 1.2 cm in thickness.

Figure 4:
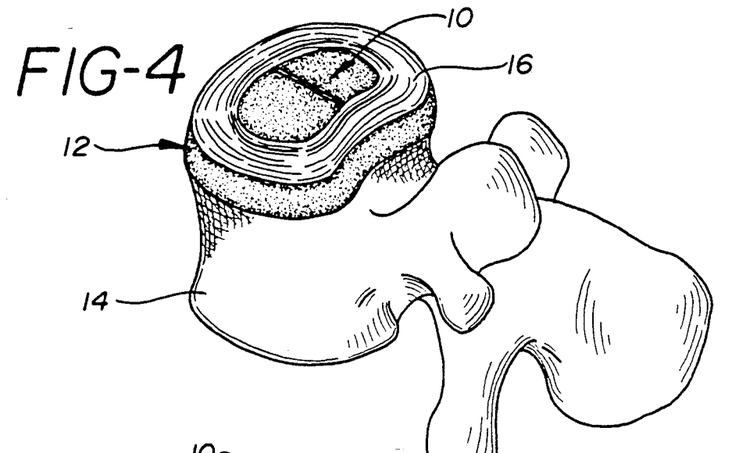
FIGS. 4 through 6 show three embodiments of a two-part prosthetic nucleus of the present invention in the hydrated state implanted within a vertebrae.
Figure 5:
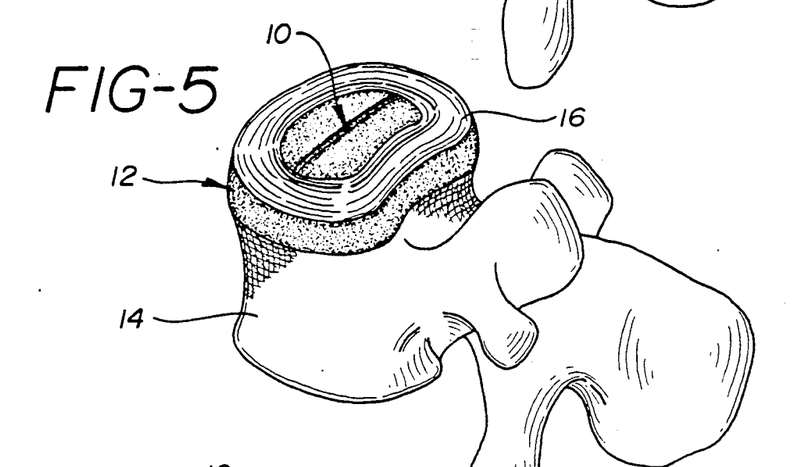
Figure 6:
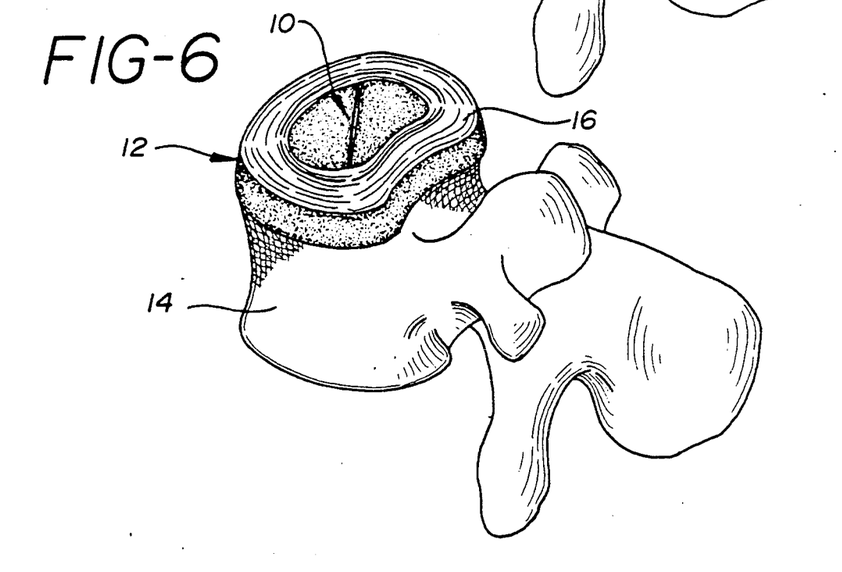

In an alternate embodiment shown in FIGS. 4-6, the prosthetic nucleus has two halves having the combined shape of a natural nucleus. Several designs of the two-part implants can be used. The first one of these is made by dividing the nucleus longitudinally (FIG. 4). The other is made by dividing the nucleus transversely (FIG. 5). Another design is to divide two halves laterally (FIG. 6). The major advantage of the two-part design is that the incision area can be further reduced and it is easier to manipulate the implants during surgery.

The surface of the implants can either be smooth or have transverse grooves (not shown) to increase the stability of the prosthesis in the disc cavity. To better fit into the vertebral body, the surface of the one piece prosthesis can be slightly convex because the surface of the vertebral body is slightly concave.

The shaped hydrogel of the present invention has a much higher structural integrity than the natural nucleus (shaped gel vs loose gel). This is because unlike the loose gel of the natural nucleus, the shaped gel has shape memory because the polymer matrix has cross-linking or strong hydrogen bonding. However, it will still have extensive lateral bulging under high compressive load if there is no boundary to constrain the deformation. Because use of the present invention does not involve any removal of the disc annulus and end-plates, the lateral bulging of the hydrogel nucleus will be restricted by the restoring force of the stretched fibers. Also, due to its superior structural integrity, the hydrogel nucleus will not herniate or bulge through the previously herniated areas or the incision which was made to remove the degenerated nucleus.

Figure 7:
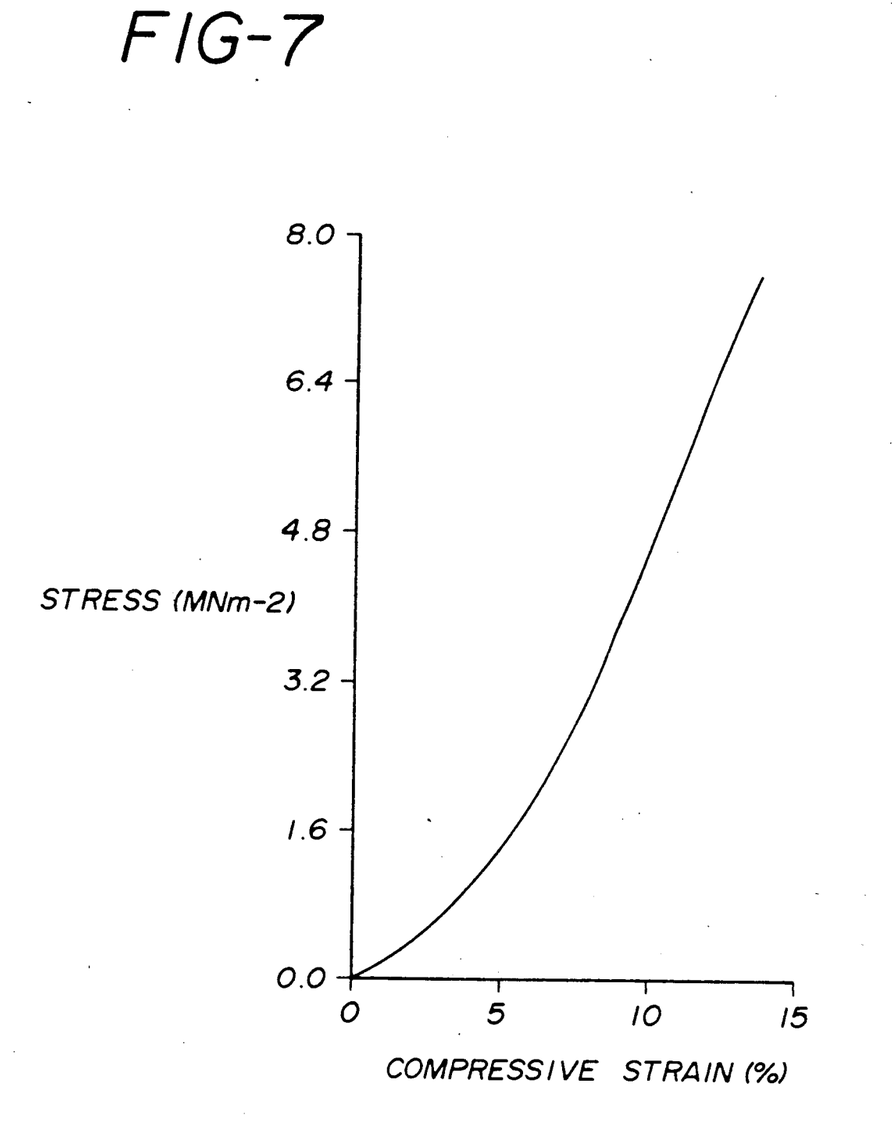
FIG. 7 is a graph showing the result of a stress vs strain test of a PVA hydrogel.

The stress vs strain curve of the PVA hydrogel of 74% water content made from 10-25% PVA powder as described above is presented in FIG. 7. To mimic the constrained environment in which the nucleus is contained, a 1.0" in diameter and 0.8" in height PVA hydrogel disc was constrained in a connected threepiece test fixture having two rigid metal sleeves on each side with a flexible Tygon tube with wall thickness of $\frac{1}{8}$" in the middle. All three pieces have an inner diameter of 1". The PVA hydrogel was then compressed in between two 1" diameter solid cylinders inserted in either end of the test fixture and compressed in an Instron ® testing machine and the stress vs strain curve was recorded. This setup, under the test stress range, would allow the hydrogel to bulge about 1-2 mm laterally, which is close to the lateral bulging reported previously in human spinal disc tests (Reuber, M., et al, Journal of Biomechanical Engineering, volume 104, 1982, p. 187). Again, the extent of directional bulging of the prosthetic nucleus of the present invention would still be largely dependent on the restoring forces of the annulus. This stress vs strain curve of the PVA hydrogel demonstrated that the PVA hydrogel offers similar or superior load resistant characteristics to the intervertebral disc. A compressive load of up to 4000N was exerted on the hydrogel, indicating that the hydrogel is strong enough to withstand a load in excess of those normally generated by the body in various postures.

Figure 8:
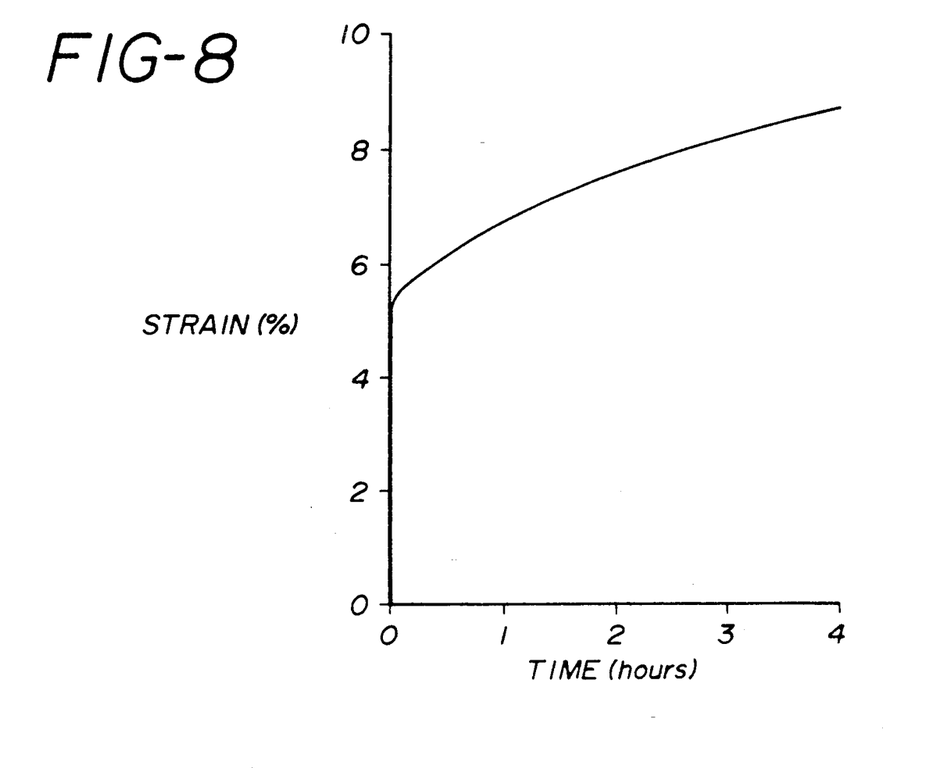
FIG. 8 is a graph showing the result of a creep test of a PVA hydrogel.
Figure 9:
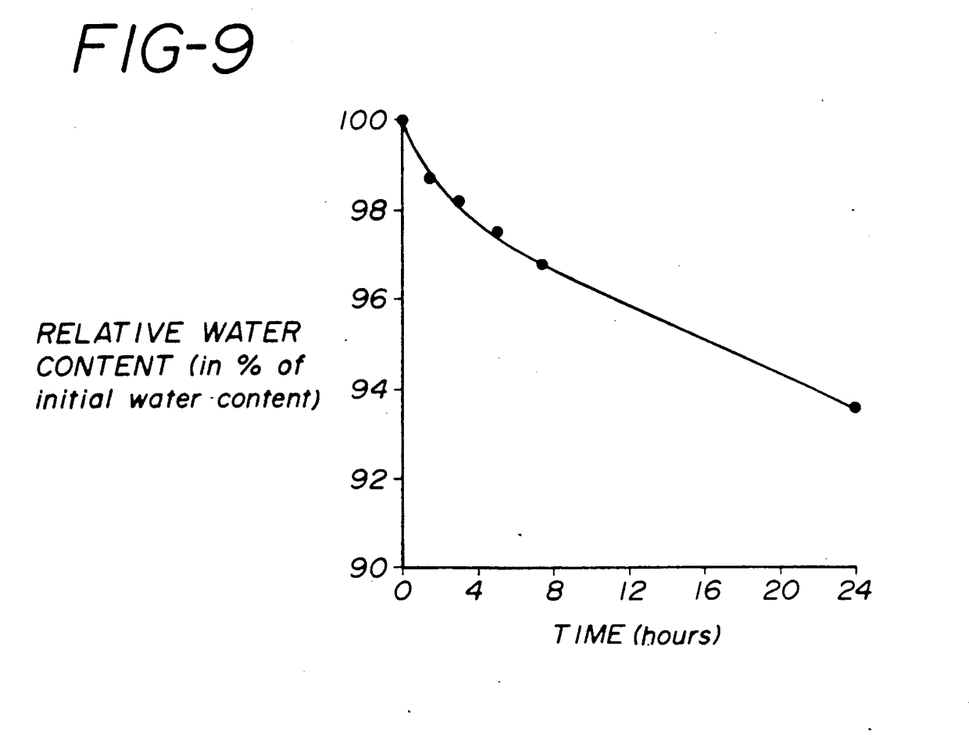
FIG. 9 is a graph showing the result of water content change vs time of a PVA hydrogel under constant compressive load.

Because the natural nucleus is also primarily a hydrogel, the implanted hydrogel artificial nucleus can easily restore all the biomechanical functions of the nucleus which has been removed. Unlike the prior art prosthetic discs, the hydrogel nucleus in the present invention will restore the visco-elastic behavior of the disc due to the water binding capability of the prosthetic hydrogel. FIG. 8 presented the creep behavior of the same PVA hydrogel of 74% water content. This hydrogel was tested in the same device as described above in the test of FIG. 7. The creep curve of the hydrogel is very similar to creep curve obtained in the human spinal disc reported elsewhere (Adam, M. A., and Hutton, W. C., The Biology of the Intervertebral Disc, Vol. II, 1988, p. 64). The initial, almost instantaneous, deformation in the disc arises mainly from a rearrangement of the collagen network in the annulus. The initial deformation in this case is mainly due to the stretching of the Tygon tube. If the load is maintained, the disc continues to deform or creep largely because the fluid in the nucleus is being squeezed out. This is shown in FIG. 9 in which the percentage of water relative to the initial water content was plotted vs time when constant load was applied. This visco-elastic characteristic, as mentioned above, is critical in withstanding the mechanical load and keeping the fluid flowing in and out of the disc.

The implantation of prosthetic nucleus 10 can be performed in conjunction with a laminectomy operation, such as discectomy or microdiscectomy, percutaneous discectomy, or chemonuclealysis. Because the properties of the hydrogel prosthetic nucleus of the present invention are similar to those of the nucleus material, the herniated nucleus can be partially or totally replaced by the hydrogel prosthetic nucleus. Due to its small size, a posterior lateral approach can be used to implant the dehydrated hydrogel disc. This significantly reduces the difficulty and the risk of the operation.

The volume of a hydrogel nucleus of 80% water content will reduce by about 80% (to 20% of its original volume) when dehydrated. Consequently, the surgeon does not need to jack apart the vertebrae adjacent to a damaged disc as required by, for example, the device disclosed in U.S. Pat. No. 4,772,287. The height of the dehydrated prosthetic nucleus, when inserted, is smaller than the disc space. Furthermore, the rigidity of the dehydrated prosthetic nucleus will help the surgeons to manipulate the prosthetic nucleus during the operation. After implantation, the hydrogel nucleus of the present invention swells slowly in the body to a predetermined height which is enough to maintain the space between the vertebral body. The swelling process normally takes several hours to two days depending on the size of the prosthetic nucleus and type of hydrogel.

While several examples of the present invention have been described, it is obvious that many changes and modifications may be made thereunto, without departing from the spirit and scope of the invention.

We claim:

1. A prosthetic nucleus for implanting in the disc space after the removal of the degenerated or damaged nucleus of an intervertebral disc comprising:
    a biologically compatible hydrogel material having when fully hydrated a size and shape generally conforming to a natural nucleus and having a water content of at least 30%, and a compressive strength of 4 MNm$^{-2}$ or greater.

2. The prosthetic nucleus as set forth in claim 1 wherein said hydrated hydrogel material has a water content of between 70 and 90%.

3. The prosthetic nucleus as set forth in claim 1 wherein the hydrogel when dehydrated has a volume of 10-70% of said hydrated hydrogel nucleus.

4. The prosthetic nucleus as set forth in claim 1 formed from at least two pieces of hydrogel material having a combined shape generally conforming to the natural nucleus.

5. The prosthetic nucleus as set forth in claim 1 wherein the hydrogel is made from a 10-25% PVA powder mixed with a solvent selected from the group consisting of water, dimethyl sulfoxide, ethylene glycol and a combination thereof.

6. The prosthetic nucleus as set forth in claim 5 wherein the hydrogel is prepared by crystallizing a solution of polyvinyl alcohol at a temperature of −10° C. or below.

7. The prosthetic nucleus as set forth in claim 1 wherein the hydrogel is prepared by the polymerization of monomers selected from the group consisting of: N-vinyl monomer (e.g. N-vinyl-2-pyrrolidone), hydroxy alkyl methacrylate (e.g. 2-hydroxylethlyl methacrylate), alkyl methacrylate (e.g. methyl methacrylate), ethylenical unsaturated and or its salt (e.g. methacrylic acid), ethylenically unsaturated base or its salt (e.g. N,N-diethyl-aminoethyl methacrylate and a combination thereof with a cross-linking monomer containing at least two ethylinic sites (e.g. ethylene glycol dimethacrylate).

8. The prosthetic nucleus as set forth in claim 1 wherein the hydrogel is made of polyacrylonitrile hydrogel.

9. The prosthetic nucleus as set forth in claim 7 wherein the hydrogel has a shape memory resulting from cross-linking the polymer with ethylene glycol.

10. A method for forming a prosthetic nucleus comprising the steps of forming a mass of bonded biocompatible hydrogel material having a water content when fully hydrated of at least 30% and a compressive strength of 4 $MNm^{-2}$ or greater; and shaping the mass of hydrogel to a shape generally conforming to a natural human disc nucleus.

* * * * *